(12) United States Patent
Kim et al.

(10) Patent No.: US 12,306,101 B2
(45) Date of Patent: May 20, 2025

(54) SUCCESSIVE OPTICAL ANALYSIS SYSTEM AND SUCCESSIVE OPTICAL ANALYSIS METHOD

(71) Applicant: VIEWORKS CO., LTD., Anyang-si (KR)

(72) Inventors: Young Ho Kim, Seoul (KR); Yu Jung Kang, Anyang-si (KR)

(73) Assignee: VIEWORKS CO., LTD., Anyang-si (KR)

( * ) Notice: Subject to any disclaimer, the term of this patent is extended or adjusted under 35 U.S.C. 154(b) by 1202 days.

(21) Appl. No.: 17/112,313

(22) Filed: Dec. 4, 2020

(65) Prior Publication Data

US 2021/0172875 A1 Jun. 10, 2021

(30) Foreign Application Priority Data

Dec. 6, 2019 (KR) .................. 10-2019-0161154

(51) Int. Cl.
*C12Q 1/6869* (2018.01)
*B01L 3/00* (2006.01)
*G01N 21/64* (2006.01)

(52) U.S. Cl.
CPC .... *G01N 21/6428* (2013.01); *B01L 3/502784* (2013.01); *C12Q 1/6869* (2013.01); *G01N 21/6486* (2013.01); *G01N 2021/6463* (2013.01); *G01N 2201/02* (2013.01); *G01N 2201/063* (2013.01)

(58) Field of Classification Search
CPC ........... G01N 21/6428; G01N 21/6486; G01N 2021/6463; G01N 2201/02; G01N 2201/063; B01L 3/502784; C12Q 1/6869
See application file for complete search history.

(56) References Cited

U.S. PATENT DOCUMENTS

| | | | |
|---|---|---|---|
| 4,732,479 A * | 3/1988 | Tanaka | G01N 15/1434 356/336 |
| 9,139,875 B2 | 9/2015 | Triener et al. | |
| 10,017,815 B2 | 7/2018 | Oliphant | |
| 2008/0260577 A1* | 10/2008 | Shirai | G01N 21/01 422/52 |
| 2011/0195406 A1* | 8/2011 | Sorenson | C12N 9/1252 703/2 |
| 2014/0118743 A1* | 5/2014 | Kao | G01N 21/253 356/432 |

(Continued)

FOREIGN PATENT DOCUMENTS

| | | | |
|---|---|---|---|
| JP | 2015512029 A | 4/2015 | |
| JP | 2015533419 A | 11/2015 | |
| KR | 20190011973 A | 2/2019 | |

(Continued)

*Primary Examiner* — Jill A Warden
*Assistant Examiner* — Michael Stanley Gzybowski
(74) *Attorney, Agent, or Firm* — Rabin & Berdo, P.C.

(57) ABSTRACT

Disclosed are a successive optical analysis system for optically analyzing a flow cell, including: at least one stage on which the flow cell is loaded; at least two optical analyzing units configured to optically analyze the flow cell loaded on the stage; and a conveying unit configured to convey at least one of the stage and the optical analyzing unit and align positions of the stage and the optical analyzing unit, and a successive optical analysis method using the same.

17 Claims, 12 Drawing Sheets

(56) References Cited

U.S. PATENT DOCUMENTS

2016/0160276 A1* 6/2016 Earney ............... G01N 21/6428
  506/13
2018/0155781 A1   6/2018 McCaffrey et al.

FOREIGN PATENT DOCUMENTS

KR        20190103267 A       9/2019
WO    WO-2018165099 A1 *   9/2018   .......... B01J 19/0046

* cited by examiner

FIG. 2
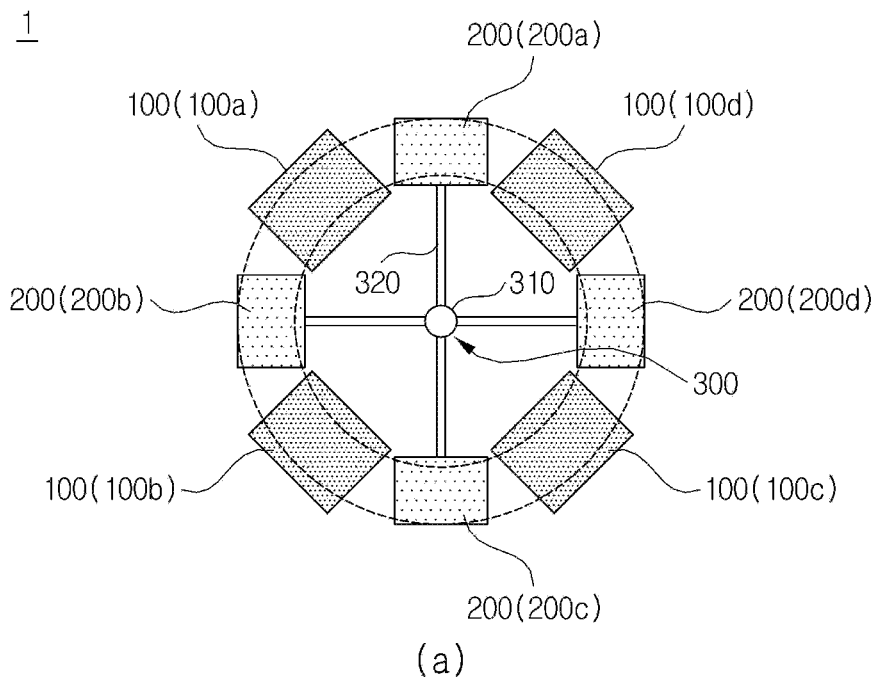
(a)
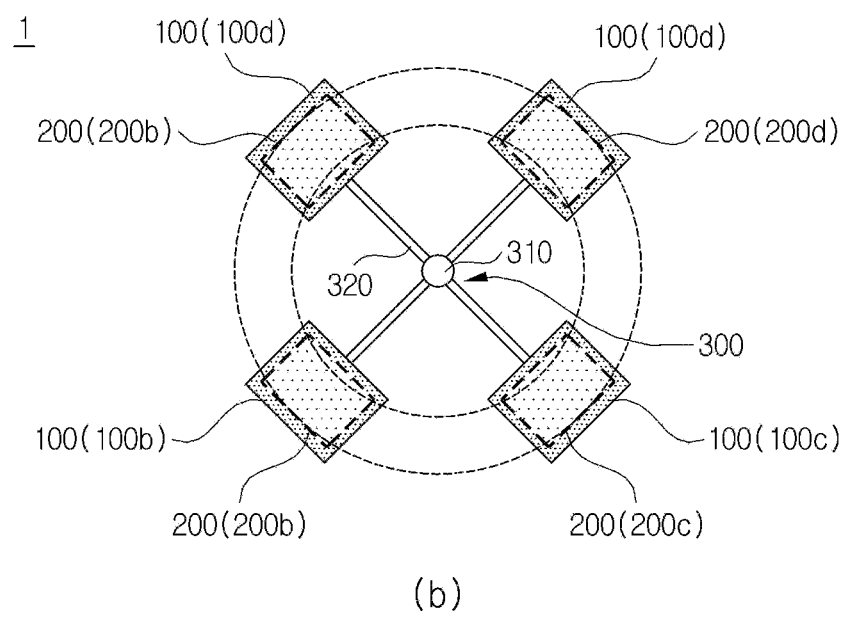
(b)

SUCCESSIVE OPTICAL ANALYSIS SYSTEM AND SUCCESSIVE OPTICAL ANALYSIS METHOD

CROSS-REFERENCE TO RELATED APPLICATIONS

This application claims priority to and the benefit of Korean Patent Application No. 10-2019-0161154 filed in the Korean Intellectual Property Office on Dec. 6, 2019, the entire contents of which are incorporated herein by reference.

TECHNICAL FIELD

The present invention relates to a successive optical analysis system and method, and more particularly, to a successive optical analysis system and method for biologically or chemically analyzing genes and the like.

BACKGROUND ART

With recent advances in scientific technology, personalized medical technology is developing that tests the expression level of a patient's gene or protein or mutation of a gene, and selects a treatment method for the patient based on the test.

Next Generation Sequencing (NGS) creates a new turning point in the gene analysis. The NGS is the method of quickly deciphering vast genome information by breaking down one genome into countless DNA fragments, reading the nucleotide sequence of each fragment at the same time, and then combining the DNA fragments by using computer technology.

An example of NGS is as follows. First, a DNA is cut into DNA fragments, and then adaptors are attached to both ends of the DNA fragment to prepare a library. The prepared DNA library is dispensed into wells of a flow cell to which complementary oligos to the adapters are attached, and the adapters linked with the DNA fragments are bound to the oligos and the DNA fragments are amplified on the flow cell. During this process, the two adapters linked to a DNA fragment attached to the two oligos on the surface of the flow cell to form a bridge, and then those DNA bridges are amplified to generate DNA clusters. Then, the base sequence is decoded by using the sequencing by synthesis that measures fluorescence that appears when a base is intervened during DNA synthesis. The base sequence deciphering is performed in the unit of a cluster. When a reaction in which a complementary base binds to the base of the DNA fragment occurs, fluorescent light of the base is emitted. Different colors of fluorescent light may be emitted for each base A, G, C, and T, and the base sequence is decoded by analyzing the image according to each reaction to determine the sequence of the bases.

However, the related NGS system is configured to simultaneously acquire a signal by the plurality of bases, so that there is a problem in that a disposition of a light source emitting excite light, an optical filter and an image sensor for separating a signal by each base, and an optical element for transmitting an optical signal is complex. Further, in acquiring an optical signal from a specific base, an optical path is formed long, so that there is a problem in that detection accuracy deteriorates. Further, the improvement of a sequencing speed is an issue that needs to be continuously improved in the NGS.

SUMMARY OF THE INVENTION

The present invention has been made in an effort to provide a successive optical analysis system which improves detection accuracy by simplifying a configuration for detecting an optical signal and decreasing noise.

The present invention has also been made in an effort to provide a successive optical analysis system which is capable of simultaneously analyzing a plurality of flow cells by successively disposing a plurality of optical analyzing units, thereby improving an analysis speed (throughput).

An exemplary embodiment of the present invention provides a successive optical analysis system for optically analyzing a flow cell, including: at least one stage on which the flow cell is loaded; at least two optical analyzing units configured to optically analyze the flow cell loaded on the stage; and a conveying unit configured to convey at least one of the stage and the optical analyzing unit and align positions of the stage and the optical analyzing unit.

In the exemplary embodiment, the stage may include a first stage and a second stage, and the second stage may be positioned in a second optical analyzing unit of the optical analyzing unit and perform a second optical analysis while the first stage is positioned in a first optical analyzing unit of the optical analyzing unit and performs a first optical analysis.

The conveying unit may include a first conveying unit which conveys the stage to the optical analyzing unit by rotating the stage.

In the exemplary embodiment, the stage may be minutely position-movable by moving in at least one straight direction or rotating by a linear motor method or a piezo method.

At least one of the stage and the optical analyzing unit may move in a vertical direction to adjust a gap between the flow cell loaded to the stage and the optical analyzing unit.

In the exemplary embodiment, the conveying unit may include a second conveying unit which conveys the optical analyzing unit to the stage side by rotating the optical analyzing unit.

In another exemplary embodiment, the conveying unit may include a convey track, and a moving conveying unit which moves the stage or the optical analyzing unit while moving along the conveying track.

In the exemplary embodiment, the successive optical analysis system may further include an analysis support unit which loads or unloads the flow cell for the stage or supplies a reagent to the flow cell.

The analysis support unit may load or unload the flow cell or supply the reagent to the flow cell for an idle stage that is not positioned in the optical analyzing unit among the stages.

In the exemplary embodiment, the optical analyzing unit may include: a light source which emits light; an optical filter which allows an optical signal of a specific wavelength band to pass through; and an optical detector which detects the optical signal, and the optical analyzing unit may be provided with a spacing to which the stage is to move and be positioned.

The spacing may be formed between the light source and the optical filter.

In at least two optical analyzing units, at least one of a wavelength band of the light source, a transmissive wavelength band of the optical filter, and a transmissive wavelength band of a light source filter provided at a light output side of the light source may be set differently.

In the exemplary embodiment, the optical analyzing unit may further include an optical mask provided with mask holes formed through a front end of the optical detector to correspond to detecting elements of the optical detector or formed to allow light to pass through.

A size of the mask hole may be smaller than a size of the detecting element, and may be smaller than a size of a reaction region of the flow cell.

A pixel size of the detecting element may be set to be the same as an interval between the reaction regions.

The reaction regions of the flow cell existing in a region photographable by the optical detector one time may be more than a combination of the detecting elements and the mask holes.

The reaction region of the flow cell may be at least divided into a first cluster group and a second cluster group adjacent to the first cluster group, and an assembly of the optical detector and the optical mask may minutely shift relative to the flow cell after detecting a fluorescent signal for the first cluster group and detect a fluorescent signal for the second cluster group.

Another exemplary embodiment of the present invention provides a successive optical analysis method using a successive optical analysis system including at least one stage, and an optical analyzing unit including a first optical analyzing unit and a second optical analyzing unit, the successive optical analysis method including: (a) loading a flow cell on the stage; (b) positioning the stage in the first optical analyzing unit by conveying at least one of the stage and the first optical analyzing unit; (c) performing, by the first optical analyzing unit, a first optical analysis on the flow cell loaded on the stage; (d) positioning the stage in the second optical analyzing unit by conveying at least one of the stage and the second optical analyzing unit; and (e) performing, by the second optical analyzing unit, a second optical analysis on the flow cell loaded on the stage.

In the exemplary embodiment, the stage may include a first stage and a second stage, and the second optical analyzing unit may perform a second optical analysis on the second stage while the first optical analyzing unit performs a first optical analysis on the first stage.

The stage may be provided in plural, and the flow cell may be loaded or unloaded or a reagent may be supplied to the flow cell for an idle stage on which an optical analysis is not performed.

The optical analyzing unit may further include a third optical analyzing unit for a third optical analysis and a fourth optical analyzing unit for a fourth optical analysis, and the first to fourth optical analyses may be sequentially performed on the flow cell loaded on the stage and a new reagent is supplied after performing the successive optical analysis or before at least one of the first to fourth optical analysis.

According to the present invention, it is possible to simplify an optical signal detection configuration and reduce noise, thereby improving detection accuracy.

According to the present invention, it is possible to continuously perform the optical analysis on the flow cell, thereby improving an analysis speed.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIG. 2 is a diagram schematically illustrating a successive optical analysis system according to an exemplary embodiment of the present invention.

Figure 1:
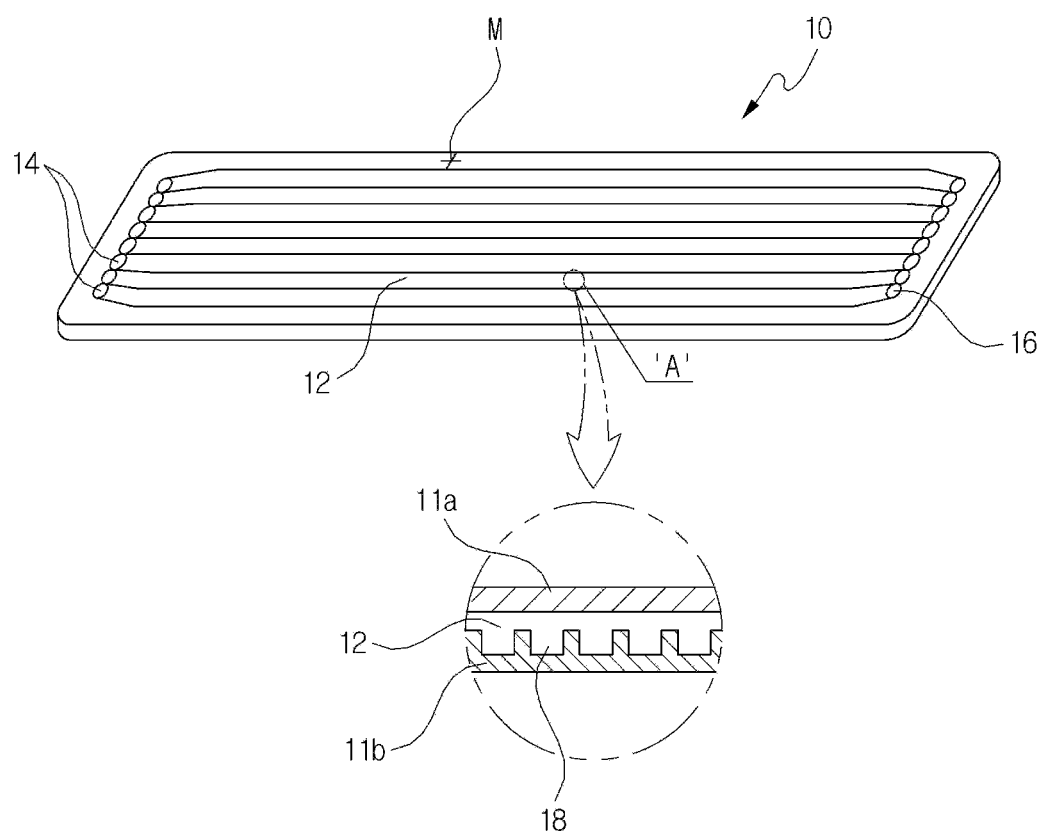
FIG. 1 is a diagram illustrating an example of a flow cell.

It should be understood that the appended drawings are not necessarily to scale, presenting a somewhat simplified representation of various features illustrative of the basic principles of the invention. The specific design features of the present invention as disclosed herein, including, for example, specific dimensions, orientations, locations, and shapes will be determined in part by the particular intended application and use environment.

In the figures, reference numbers refer to the same or equivalent parts of the present invention throughout the several figures of the drawing.

DETAILED DESCRIPTION

Hereinafter, exemplary embodiments of the present invention will be described in detail with reference to the accompanying drawings. First of all, it should be noted that in giving reference numerals to elements of each drawing, like reference numerals refer to like elements even though like elements are shown in different drawings. Further, in the following description of the present invention, a detailed description of known configurations or functions incorporated herein will be omitted when it is judged that the detailed description may make the subject matter of the present disclosure unclear. It should be understood that although the exemplary embodiment of the present invention is described hereafter, the spirit of the present invention is not limited thereto and the present invention may be changed and modified in various ways by those skilled in the art.

A successive optical analysis system and a successive optical analysis method according to the present invention are for a biological or chemical optical analysis and may be utilized in, for example, sequencing DNA (deoxyribonucleic acid). Hereinafter, the present invention will be described based on DNA sequencing, but the technical spirit of the present invention is not limited to the DNA sequencing.

FIG. 1 is a diagram illustrating an example of a flow cell, and an enlarged cross-section of portion A of FIG. 1 is also illustrated.

A flow cell 10 is provided with at least one fluid channel 12, and a plurality of wells 18 functioning as a reaction region is formed in the fluid channel 12. DNA fragments may be attached to the plurality of wells 18 while forming a cluster. The plurality of wells 18 may be formed in various patterns, such as a grid form or a zigzag form. The fluid channel 12 is connected with an inlet 14 for supplying a reagent containing a base that complementarily binds to the DNA clusters and an outlet 16 for discharging the reagent.

The flow cell 10 may be formed of a base panel 11b forming a lower structure and a cover 11a covering an upper portion of the fluid channel 12. Further, the base panel 11b and the fluid channel 12 may be formed of a light transmitting material. For the DNA sequencing, the well 18 of the flow cell 10 may be prepared in the state where the DNA cluster is attached to the well 18.

In the exemplary embodiment, an align mark M may be formed in the flow cell 10. The align mark M may be a reference for aligning the flow cell 10 during the optical analysis. The align mark M illustrated in FIG. 1 is merely an example, and it is also possible to change the location of the align mark M or increase the number of align marks M as necessary.

FIG. 2 is a diagram schematically illustrating a successive optical analysis system according to an exemplary embodiment of the present invention. (a) of FIG. 2 illustrates a state where the stage 200 is not located at the optical analyzing unit 100 side and (b) of FIG. 2 illustrates a state where the stage 200 is located at the optical analyzing unit 100 side.

A successive optical analysis system 1 according to the present invention includes at least two optical analyzing units 100 which are sequentially disposed, a plurality of stages 200 for loading the flow cell 10, and a first conveying unit 300 for adjusting a relative position of the plurality of stages 200 and the optical analyzing units 100.

It is exemplified that four optical analyzing units 100a, 100b, 100c, and 100d are disposed in a circular form in the successive optical analysis system 1 illustrated in FIG. 2. However, in the implementation of the present invention, the number of optical analyzing units 100 may be 2, 3, or more. Further, the plurality of optical analyzing units 100a, 100b, 100c, and 100d may also be sequentially disposed in the form of a straight line or curved line, not a circular form.

The optical analyzing unit 100 performs an optical analysis on the flow cell 10. In the exemplary embodiment, each optical analyzing unit 100 is set to acquire a specific fluorescent signal generated by a base complementarily binding to a DNA cluster provided in the flow cell 10. Particularly, the first optical analyzing unit 100a may be configured to acquire an optical signal by adenine (A), the second optical analyzing unit 100b may be configured to acquire an optical signal by cytosine (c), the third optical analyzing unit 100c may be configured to acquire an optical signal by guanine (G), and the fourth optical analyzing unit 100d may be configured to acquire an optical signal by thymine (T). To this end, each of the first to fourth optical analyzing units 100a, 100b, 100c, and 100d may be provided with a light source and an optical filter for acquiring the corresponding optical signal.

The stage 200 is configured to load the flow cell 10. The stage 200 may be provided in plural including first to fourth stages 200a, 200b, 200c, and 200d according to the number of optical analyzing units 100. However, in the implementation of the present invention, the number of stages 200 is not limited thereto, and may be increased/decreased as necessary. Further, FIG. 2 illustrates the example in which the optical analyzing units 100a, 100b, 100c, and 100d and the stages 200a, 200b, 200c, and 200d are disposed in a circular shape while forming an angle of 90°, but the angular arrangement may be changed as necessary.

The stage 200 may be configured to be driven in at least one axis direction in order to align a position of the flow cell 10 in a relationship with the analyzing unit 100 in the state where the flow cell 10 is loaded. The stage 200 may include a linear motor or may be minutely driven by a piezo method.

When the light source which is provided in the optical analyzing unit 100 and emits light to the flow cell 10 is located in an upper portion of the stage 200, the stage 200 may be configured in the form of a plate supporting the flow cell 10 in a lower portion.

As another exemplary embodiment, when the light source emitting light to the flow cell 10 is located in a lower portion of the stage 200, the stage 200 may have the configuration capable of transmitting light to the flow cell 10. For example, the stage 200 may include a piezo stage which is formed with an aperture and is capable of XY positioning like models P-541 and P-542 of Physik Instrumente (PI) GmbH & Co.

The stage 200 may also be configured to be driven in a height direction (Z-axis) to adjust a height of the flow cell 10. Further, the minute driving stage in the piezo method may be configured to be rotatable based on at least one axis among the X, Y, and Z axes through a rotation to adjust an angle in a plane.

In another exemplary embodiment, the stage 200 may also be configured to be conveyed to the optical analyzing unit 100 in the state where the flow cell 10 is supported on the stage 200, the optical analyzing unit 100 checks a position of the flow cell 10, and a partial configuration of the optical analyzing unit 100 is position-adjusted in accordance with the position of the flow cell 10. In this case, the optical analyzing unit 100 may be configured to be additionally provided with a linear motor or a minute driving means in the piezo method to be linearly or rotationally driven in at least one axis direction. In the exemplary embodiment, the position alignment of the optical analyzing unit 100 and the flow cell 10 may be performed by recognizing the align mark M formed in the flow cell 10 as described above.

In the exemplary embodiment of FIG. 2, the first conveying unit 300 is configured to convey the stage 200 to the optical analyzing unit 100. In the exemplary embodiment, the first conveying unit 300 may include a first rotation driving unit 310, and a first support frame 320 of which one side is connected to the first rotation driving unit 310 and the other side is connected to the stage 200. The stage 200 connected to the first support frame 320 by the first rotation driving unit 310 may rotate (in a counterclockwise direction) and sequentially move from the first optical analyzing unit 100a to the fourth optical analyzing unit 100d.

In describing a process of performing an optical analysis on the flow cell 10, the flow cell 10 attached with the DNA cluster is loaded on the first stage 200a, the first conveying unit 300 is driven, and the first stage 200a moves to the first optical analyzing unit 100a. The first optical analyzing unit 100a detects an optical signal according to a first base (for example, adenine (A)). After the optical analysis in the first optical analyzing unit 100a is completed, the first conveying unit 300 is driven and the first stage 200a moves to the second optical analyzing unit 100b to detect an optical signal by a second base (for example, cytosine (C)). By the method, the first stage 200a sequentially moves to the third optical analyzing unit 100c and the fourth optical analyzing unit 100d to detect optical signals according to a third base (for example, guanine (G)) and a fourth base (for example, thymine (T)).

As the plurality of stages 200 is provided, the optical analysis may be performed in each of the plurality of optical analyzing units 100 and an optical analysis speed may be improved. As described later, in order for each optical analyzing unit 100 to perform the optical analysis for a specific base, each optical analyzing unit 100 may be provided with an optical filter which selectively transmits or blocks light in a specific wavelength band. As another exemplary embodiment, each optical analyzing unit 100 may be provided with a light source which emits light at a specific wavelength band. Further, the light source and the optical filter in each optical analyzing unit 100 may be differently set.

Figure 3:
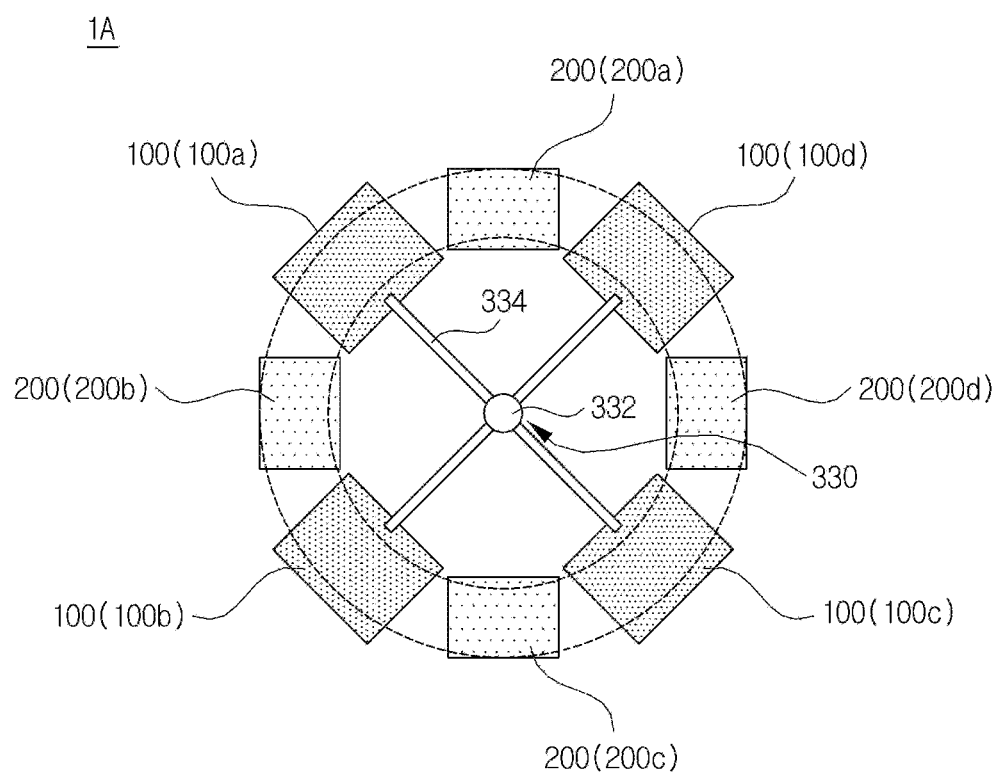
FIG. 3 is a diagram schematically illustrating a successive optical analysis system according to another exemplary embodiment of the present invention.

FIG. 3 is a diagram schematically illustrating a successive optical analysis system according to another exemplary embodiment of the present invention.

The basic configurations of FIG. 3 are the same as the configurations illustrated in FIG. 2. However, a successive optical analysis system 1A according to the exemplary embodiment of FIG. 3 is different from the exemplary embodiment of FIG. 2 in that an optical analyzing unit 100 moves, not a stage 200, so that the stage 200 is located within the optical analyzing unit 100. To this end, a second conveying unit 330 is provided for driving the optical analyzing unit 100. The second conveying unit 330 may include a second rotation driving unit 332, and a second support frame 334 of which one side is connected to the second rotation driving unit 332 and the other side is connected to the stage 200.

Summarizing the exemplary embodiments described with reference to FIGS. 2 and 3, the successive optical analysis system according to the present invention includes the plurality of optical analyzing units 100 and the plurality of stages 200, and performs an optical analysis by positioning the stage 200 within the optical analyzing unit 100 by adjusting a relative position by driving any one of the optical analyzing unit 100 and the stage 200. Herein, the stage 200 is conveyed by the first conveying unit 300 or the optical analyzing unit 100 is conveyed by the second conveying unit 330.

In the implementation of the present invention, the successive optical analysis system may be configured so that both the first conveying unit 300 and the second conveying unit 330 are provided, so that both the stage 200 and the optical analyzing unit 100 are movable. Further, for the more fine position adjustment, the successive optical analysis system may be configured so as to enable any one of the first conveying unit 300 and the second conveying unit 330 to larger position-move, and enable the other one to be minutely position-adjusted.

In the exemplary embodiment, after the optical analyzing unit 100 moves to the stage 200 by the second conveying unit 330, the stage 200 may be minutely position-adjusted by minute driving (rotation) of the first conveying unit 300. In this case, along with the rotation of the first conveying unit 300, a position between the optical analyzing unit 100 and the flow cell 10 may additionally aligned by the minute driving of the stage 200 itself using the linear motor or the piezo method or the minute driving of the optical analyzing unit 100.

In another exemplary embodiment, after the stage 200 is positioned in the optical analyzing unit 100, a position between the optical analyzing unit 100 and the flow cell 10 may be aligned by the minute driving (rotation) of the second conveying unit 330. Further, even in this case, along with the rotation of the first conveying unit 300, a position between the optical analyzing unit 100 and the flow cell 10 may be additionally aligned by the minute driving of the stage 200 itself using the linear motor or the piezo method or the minute driving of the optical analyzing unit 100.

In the examples of FIGS. 2 and 3, it is described that the first conveying unit 300 and the second conveying unit 330 adopt the rotation driving method, but as long as the stage 200 or the optical analyzing unit 100 is conveyed, various methods, such as a linear moving method or a method of moving the stage 200 or the optical analyzing unit 100 by using a clamp or a chuck, rather than the rotation driving method may be applied.

In the examples of FIGS. 2 and 3, it has been described that all of the stages 200 are conveyed together by the first conveying unit 300 and all of the optical analyzing units 100 are conveyed together with the second conveying unit 330. However, in the implementation of the present invention, the first conveying unit 300 may be configured to individually convey each stage 200, and the second conveying unit 330 may be configured to individually convey each optical analyzing unit 100.

Figure 4:
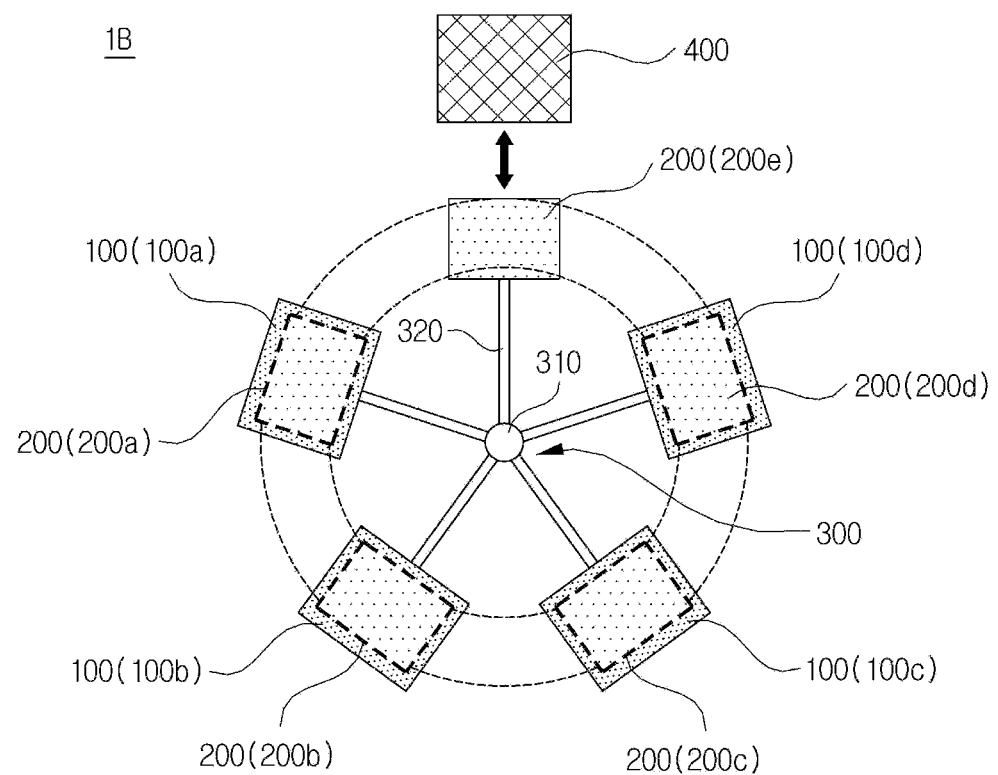
FIG. 4 is a diagram schematically illustrating a successive optical analysis system according to still another exemplary embodiment of the present invention.

FIG. 4 is a diagram schematically illustrating a successive optical analysis system according to still another exemplary embodiment of the present invention.

The exemplary embodiment illustrated in FIG. 4 illustrates an example of a successive optical analysis system 1B in which four optical analyzing units 100a, 100b, 100c, and 100d, five stages 200a, 200b, 200c, 200d, and 200e, and a conveying unit 300 are provided. The five stages 200a, 200b, 200c, 200d, and 200e are disposed while having an angle of 72°, and the optical analyzing units 100a, 100b, 100c, and 100d are disposed to simultaneously perform an optical analysis on four stages 200a, 200b, 200c, and 200d among the five stages 200a, 200b, 200c, 200d, and 200e. In the configuration, the remaining fifth stage 200e is in an idle state. A preparation operation for the optical analysis may progress for the fifth stage 200e, such as loading a new flow cell 10 to the fifth stage 200e, or supplying a new reagent to the flow cell 10 that is already loaded on the fifth stage 200e. To this end, the optical analysis system 1B may additionally include an analysis support unit 400. The analysis support unit 400 may include a flow cell loading unit which loads or unloads the flow cell 10 for the stage 200 and/or a reagent supply unit which supplies a reagent to the flow cell 10.

In the configuration according to FIG. 4, an optical analysis may more rapidly progress by progressing the analysis preparation operation for any one flow cell 10 and performing the optical analysis on other flow cells. Further, in the exemplary embodiment of FIG. 4, it is illustrated that the stage 200 is conveyed by the first conveying unit 300, but like the exemplary embodiment of FIG. 3, the second conveying unit 330 may be provided to convey the optical analyzing unit 100, or both the first conveying unit 300 and the second conveying unit 330 may also be provided.

In the foregoing, the four optical analyzing units 100a, 100b, 100c, and 100d and the five stages 200a, 200b, 200c, 200d, and 200e are exemplified, but the number of optical analyzing units 100 may be two or more, and the stages 200 may be provided at least one or more than the number of optical analyzing units 100. Further, when the specific idle stages 200 are two or more, the flow cell may be loaded/unloaded for any one idle stage, and a new reagent may be supplied to another idle stage.

Figure 5:
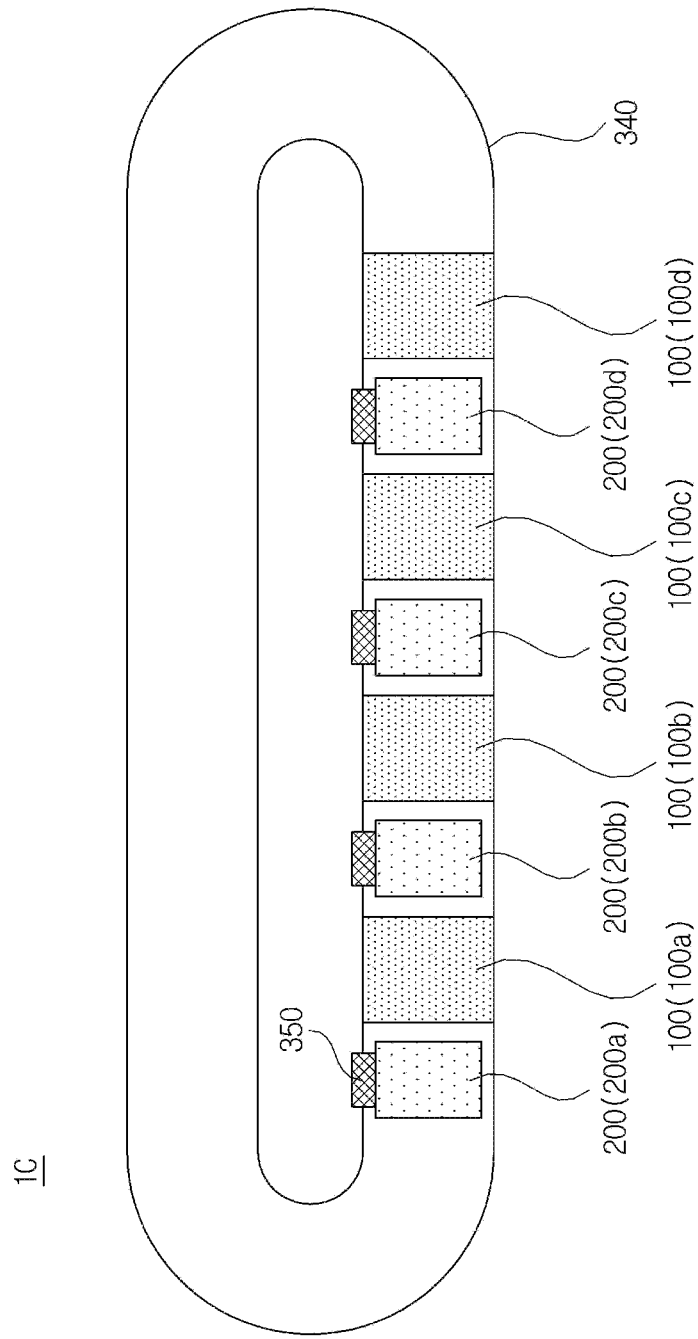
FIG. 5 is a diagram schematically illustrating a successive optical analysis system according to still another exemplary embodiment of the present invention.

FIG. 5 is a diagram schematically illustrating a successive optical analysis system according to still another exemplary embodiment of the present invention.

In a successive optical analysis system 1C illustrated in FIG. 5, a plurality of optical analyzing units 100a, 100b, 100c, and 100d are arranged in a line. A plurality of stages 200a, 200b, 200c, and 200d may be conveyed in a line to be sequentially conveyed to the optical analyzing units 100a, 100b, 100c, and 100d.

The stage 200 may be conveyed by a conveying track 340 and a moving conveying unit 350 which fixes the stage 200 and moves along the conveying track 340. The moving conveying unit 350 may be configured to sequentially convey the stage 200 to the first to fourth optical analyzing units 100a, 100b, 100c, and 100d, move along the conveying track 340, and return to the first optical analyzing unit 100a. In the exemplary embodiment, the moving conveying unit 350 may be configure by using a linear motor.

In the exemplary embodiment exemplified in FIG. 5, the optical analyzing unit 100 may be conveyed along the conveying track 340 by the moving conveying unit 350 in the state where the stage 200 is fixed.

Next, the configuration of the optical analyzing unit 100 and a relationship with the stage 200 for the optical analysis in the optical analyzing unit 100 will be described.

Figure 6:
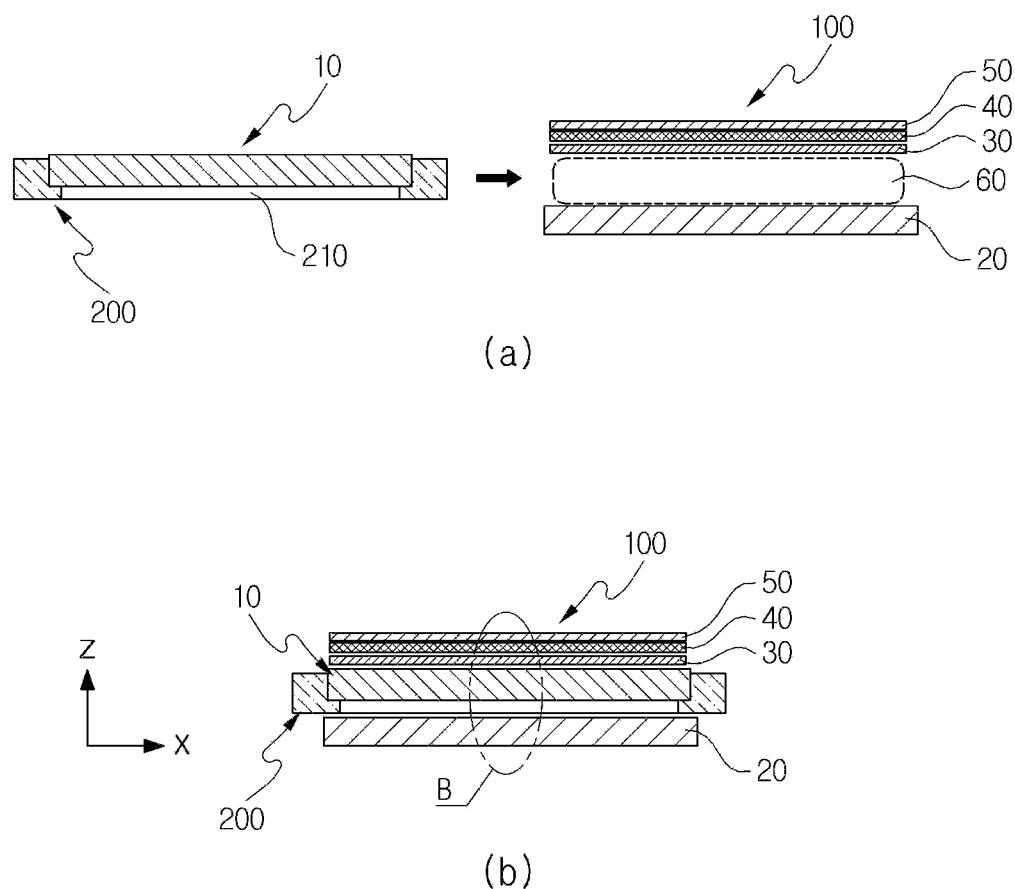
FIG. 6 is a diagram illustrating a relationship between an optical analyzing unit and a stage (flow cell) in the successive optical analysis system according to another exemplary embodiment of the present invention.
Figure 7:
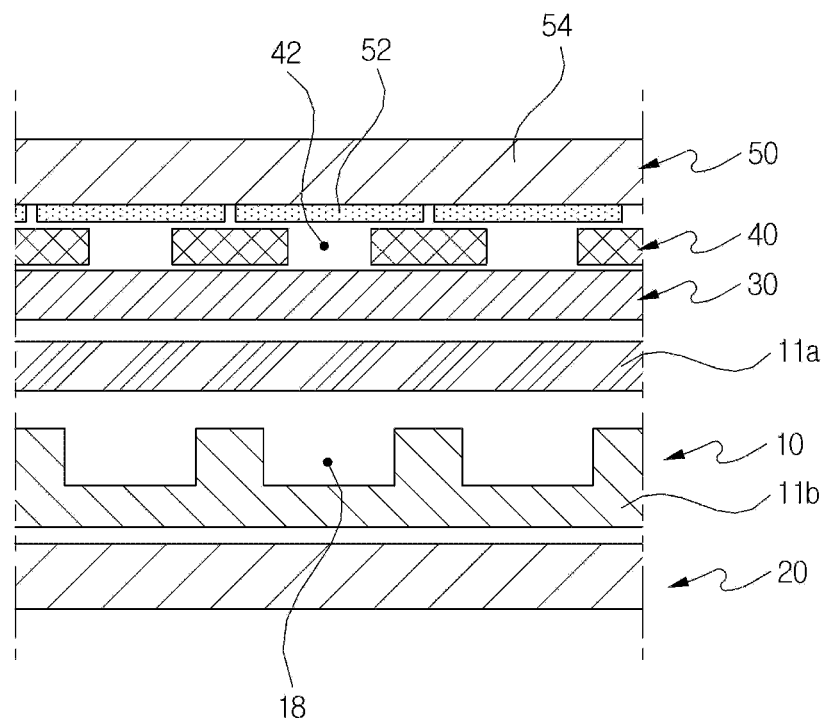
FIG. 7 is a diagram (an enlarged cross-sectional view of portion B of FIG. 6) illustrating a detailed configuration of the optical analyzing unit and the flow cell in the successive optical analysis system according to the exemplary embodiment of the present invention.
Figure 8:
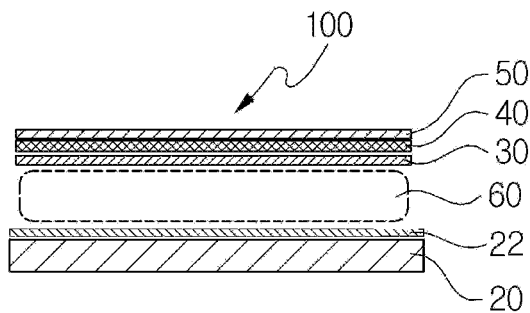
FIG. 8 is a diagram illustrating another configuration of the optical analyzing unit in the successive optical analysis system according to the exemplary embodiment of the present invention.

FIG. 6 is a diagram illustrating a relationship between the optical analyzing unit and the stage (flow cell) in the successive optical analysis system according to the exemplary embodiment of the present invention, and FIG. 7 is a diagram (an enlarged cross-sectional view of portion B of FIG. 6) illustrating a detailed configuration of the optical analyzing unit and the flow cell in the successive optical analysis system according to the exemplary embodiment of the present invention. Further, FIG. 8 is a diagram illustrating another configuration of the optical analyzing unit in the successive optical analysis system according to the exemplary embodiment of the present invention.

Referring to (a) of FIG. 6, the stage 200 is in the state where the flow cell 10 is loaded, and the stage 200 does not move to a spacing 60 of the optical analyzing unit 100.

The stage 200 may be formed with an aperture 210, and the flow cell 10 is exposed in a vertical direction through the aperture 210.

The optical analyzing unit 100 includes a light source 20 which emits light for fluorescently analyzing the DNA cluster attached to the flow cell 10, and an optical detector 50 which converts an optical signal to an electric signal. Further, the optical analyzing unit 100 may further include an optical filter 30 for allowing only an optical signal in a specific wavelength band to pass through. Further, the optical analyzing unit 100 may include an optical mask 40 for reducing noise when an optical signal is acquired. The spacing 60 in which the stage 200 may be positioned is formed between the light source 20 and the optical detector 50 of the optical analyzing unit 100 (between the light source 20 and the optical filter 30 in the case where the optical filter 30 is provided).

When the stage 200 is conveyed by the first conveying unit 300, the optical analyzing unit 100 is conveyed by the second conveying unit 330, or the stage 200 or the optical analyzing unit 100 is conveyed by the moving conveying unit 350 as described above, the stage 200 is positioned in the spacing 60 of the optical analyzing unit 100 like (b) of FIG. 6. The flow cell 10 loaded on the stage 200 and the optical detector 50 or the optical mask 40 are aligned with each other. In the exemplary embodiment, when the stage 200 is configured to be movable in at least one direction in an XY plane or the Z-axis direction by the piezo method, the position of the flow cell 10 may be adjusted by the driving of the stage 200. After the stage 200 or the optical analyzing unit 100 moves to a signal detection position by the first conveying unit 300 or the second conveying unit 330 and is aligned for the detection of a fluorescent signal, at least one of the stage 200 and the optical analyzing unit 100 may move in a vertical direction so as to adjust a gap between the stage 200 and the optical analyzing unit 100. Through this, when the signal is detected, the gap between the stage 200 and the optical analyzing unit 100 may be adjusted to a gap in which the signal is most efficiently detected.

In the exemplary embodiment, the light source 20 is positioned at an opposite side of the optical detector 50 with the spacing 60 interposed therebetween. The light source 20 may be disposed in the lateral portion of the optical detector 50 or coaxially disposed with the optical detector 50, but when the light source 20 is disposed as illustrated in FIG. 6, there is an advantage in that it is possible to simplify a disposition structure of the light source 20. In the exemplary embodiment, the light source 20 may be provided as a surface light source. Further, in the exemplary embodiment, the light source 20 may be provided in the form of an optical waveguide, and light generated from a separate light generator may be transmitted through the optical waveguide and light may be emitted to the flow cell 10. However, in the implementation of the present invention, the light source 20 is not limited to the surface light source, and may be configured as a line light source or a point light source. The light source 20 may generate light in a specific wavelength band or generate light in a plurality of wavelength bands, or may be white light. Each optical analyzing unit 100 may be able to detect and analyze a specific optical signal according to a wavelength band of light generated in the light source 20 or a combination of the light source 20 and the optical filter 30.

Referring to FIG. 8, in the light source 20, a light source filter 22 for selectively transmitting only light in a specific wavelength band may be provided at a light output side of the light source 20.

Referring to FIG. 7, the optical detector 50 may include a substrate 54 and a plurality of detecting elements 52 formed in the substrate 54. The detecting element 52 detects a fluorescent signal, and converts a fluorescent signal into an electric signal. The detecting element 52 may be implemented by a CCD or CMOS method to form one pixel. Further, the optical detector 50 may be implemented in an image sensor in which the plurality of detecting elements (that is, pixels) is arranged in an array form. When the optical detector 50 is implemented with the image sensor in which the plurality of pixels is arranged in the array form, a fluorescent signal is detected by each pixel and a detection result of the fluorescent signal may be obtained as one or more images.

The optical detector 50 may be configured such that a plurality of image sensors is disposed in succession to cover all of the wells 18 of the flow cell 10 at once. However, in the implementation of the present invention, the optical detector 50 may have an area capable of covering only a partial region of the flow cell 10, and it is possible to detect optical signals for the wells 18 of the flow cell 10 while the element including the optical detector 50 moves.

The optical mask 40 includes mask holes 42 formed to penetrate while corresponding to the detecting elements 52 or formed to allow light to pass through, and a portion except for the mask holes 42 is formed of a material through which light does not pass. The optical mask 40 may be formed in a flat plate shape in which the plurality of mask holes 42 is formed. In the exemplary embodiment, the mask hole 42 of the optical mask 40 may be formed to be smaller than the pixel size of the detecting element 52. A fluorescent signal in a specific well 18 may be incident based on a center of the detecting element 52 by the mask hole 42. The mask hole 42 may be formed in a quadrangular shape, but may also be provided in a shape of a circle, a triangle, and the like, not a quadrangle. The optical mask 40 allows the fluorescent signal in the specific well 18 to be transmitted to the corresponding detecting element 52 and prevents the fluorescent signal from the surrounding well 18 from being incident. In the exemplary embodiment, the size of the mask hole 42 may be formed to be smaller than the size of the well 18.

In the exemplary embodiment, the optical detector 50 and the optical mask 40 may be prepared while being combined with each other in the state where the detecting elements 52 and the mask holes 42 are disposed while matching to each other.

In another exemplary embodiment, the optical detector 50 and the optical mask 40 may be prepared while being combined with each other in the state where the detecting elements 52, the mask holes 42, and the filters 30 are disposed while matching to one another.

Figure 9:
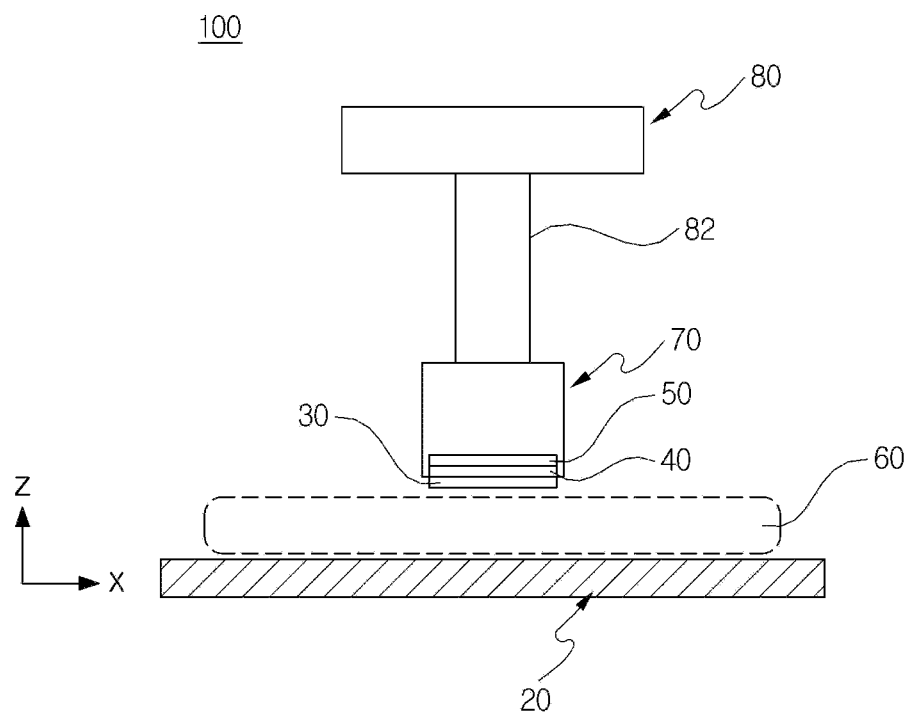
FIG. 9 is a diagram illustrating an exemplary embodiment of the optical analyzing unit in the successive optical analysis system according to the exemplary embodiment of the present invention.

FIG. 9 is a diagram illustrating an exemplary embodiment of the optical analyzing unit in the successive optical analysis system according to the exemplary embodiment of the present invention.

In the exemplary embodiment illustrated in FIG. 9, a detection range of an optical detector 50 is smaller than a size of a flow cell 10. Accordingly, the optical detector 50 detects an optical signal while moving the flow cell 10.

Referring to FIG. 9, an optical analyzing unit 100 may include a head unit 70 and a driving unit 80 for driving the head unit 70. The head unit 70 is provided with an optical filer 30, an optical mask 40, and the optical detector 50. The driving unit 80 is an element for driving the head unit 70 in at least one direction, and may be formed by a driving means, such as a linear motor. The driving unit 80 may be connected with the head unit 70 through a head unit supporting unit 82. The driving unit 80 may move the head unit 70 in at least one direction of a horizontal direction and a vertical direction (Z-axis direction).

In the exemplary embodiment, the driving unit 80 may be connected to the second conveying unit 330 described with reference to FIG. 3.

Figure 10:
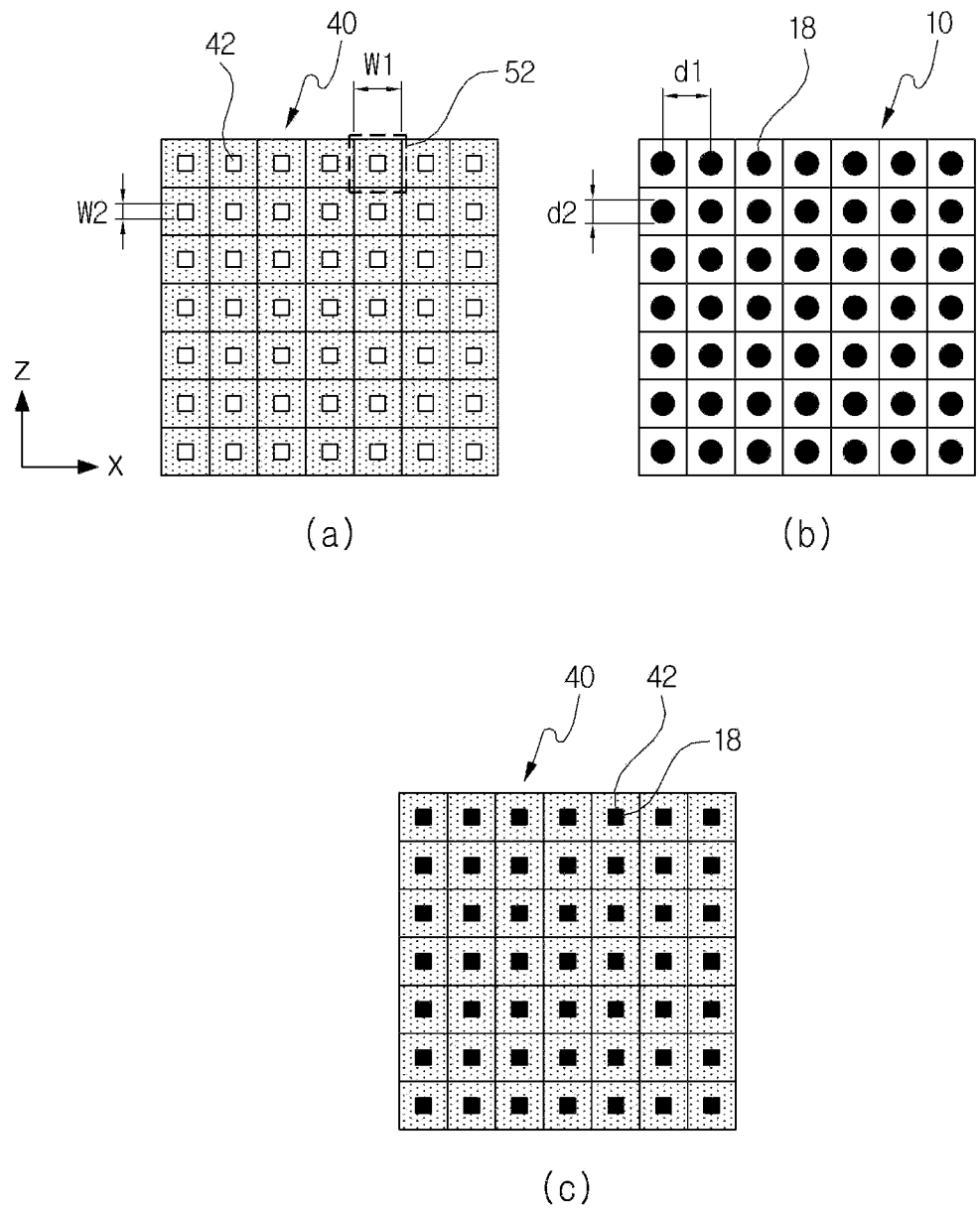
FIG. 10 is a diagram illustrating a location relationship between an optical mask of the optical analyzing unit and a well (cluster) of the flow cell in the successive optical analysis system according to the exemplary embodiment of the present invention.

FIG. 10 is a diagram illustrating a location relationship between the optical mask of the optical analyzing unit and the well (cluster) of the flow cell in the successive optical analysis system according to the exemplary embodiment of the present invention.

(a) of FIG. 10 illustrates the optical mask 40 formed with the mask holes 42. In each mask hole 42 of the optical mask 40, the detecting element 52 corresponding to the mask hole 42 is located. (a) of FIG. 10, a pixel size of the detecting element 52 is w1 and a size (a diameter in the case where the mask hole 42 has a circular shape) of the mask hole 42 is w2. w2 is smaller than w1. The fluorescent signal from the periphery of the specific well 18 may be prevented from spreading to the specific detecting element 52 by the mask hole 42. The center of the mask hole 42 may be disposed to be matched with the center of the detecting element 52.

(b) of FIG. 10 illustrates the disposition of the plurality of wells 18 formed in the flow cell 10. An interval between the adjacent wells 18 is d1 and a size (or a diameter) of the well 18 is d2. The interval d1 between the wells 18 may be defined with a distance between the centers of the adjacent wells 18. In the implementation of the present invention, the pixel size w1 may be the same or approximately the same as the interval d1 between the wells 18. The size w2 of the mask hole 42 may be smaller than the size d2 of the well 18. In the case where the size w2 of the mask hole 42 is formed to be smaller than the size d2 of the well 18, it is possible to further prevent an inflow of noise in addition to the fluorescent signal from the specific well 18.

(c) of FIG. 10 illustrates a state where the optical mask 40 is disposed in upper portions of the wells 18 of the flow cell 10.

(a) to (c) of FIG. 10 illustrate the examples in which the mask holes 42 are formed in the form of 7×7, but the number of mask holes 42 may be increased according to an actual size of the optical mask 40, and the disposition of the mask holes 42 may also be variously changed.

When the optical analyzing unit 100 is configured as illustrated in FIG. 9, after a detection of a fluorescent signal is completed for a region of the flow cell 10 corresponding to a photographing possible region of the optical detector 50, the head unit 70 may move to a not-photographed region of the flow cell 10 and then the detection of the fluorescent signal for the region may be performed.

Figure 11:
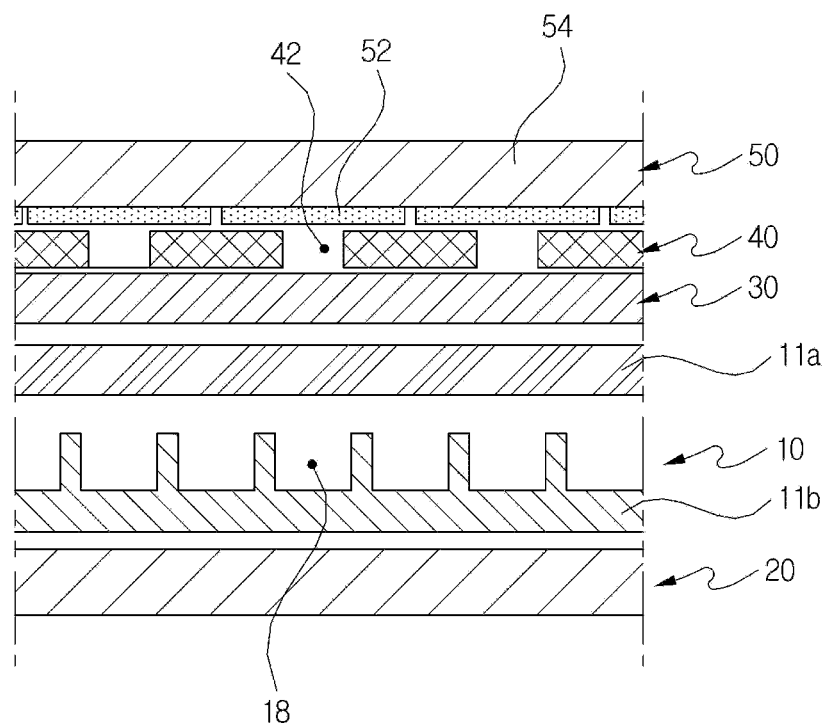
FIG. 11 is a diagram (an enlarged cross-sectional view of portion B of FIG. 6) illustrating a detailed configuration of another form of the optical analyzing unit and the flow cell in the successive optical analysis system according to the exemplary embodiment of the present invention.
Figure 12:
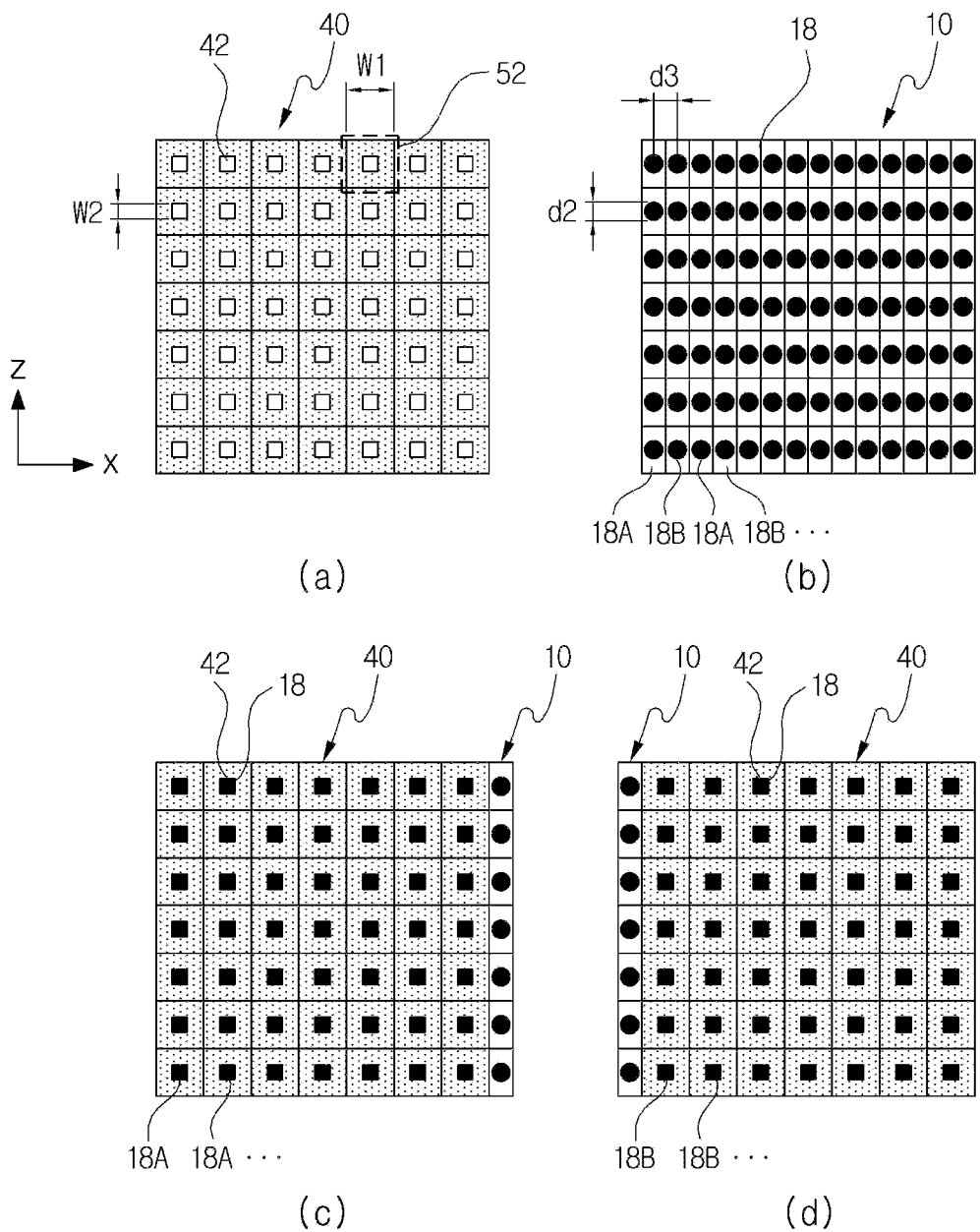
FIG. 12 is a diagram illustrating a location relationship between the optical mask and the well (cluster) of the flow cell in the configuration illustrated in FIG. 11.

FIG. 11 is a diagram (an enlarged cross-sectional view of portion B of FIG. 6) illustrating a detailed configuration of another form of the optical analyzing unit and the flow cell in the successive optical analysis system according to the exemplary embodiment of the present invention, and FIG. 12 is a diagram illustrating a location relationship between the optical mask and the well (cluster) of the flow cell in the configuration illustrated in FIG. 11.

Referring to FIGS. 11 and 12, the configuration is different from the configuration of FIGS. 7 and 10 in that the number of wells 18 is larger than each number of detecting elements 52 and mask holes 42. FIGS. 10 and 11 exemplify the case where the number of wells 18 in a region covered by the optical detector 50 is two times the number of detecting element 52 and mask holes 42. However, in the implementation of the present invention, the number of wells 18 may be the larger than the number of optical detectors 50 and mask holes 42. For example, the number of optical detectors 50 may be three or four or more times the number of mask holes 42.

(a) of FIG. 12 illustrates the optical mask 40 in which the mask holes 42 are formed, and (b) of FIG. 12 illustrates the disposition of the plurality of wells 18 formed in the flow cell 10 in which the wells 18 are disposed in 14 columns in the transverse direction.

Referring to (b) of FIG. 12, from the left column, first cluster groups 18A and second cluster groups 18B are alternately disposed. In this case, a distance between the first cluster group 18A and the second cluster group 18B is d3, and d3=(w1)/2.

(c) of FIG. 12 illustrates a detection of a fluorescent signal for the first cluster group 18A and (d) of FIG. 12 illustrates a detection of a fluorescent signal for the second cluster group 18B.

Referring to (c) of FIG. 12, a head unit 40 is located relative to the flow cell 10 so that the fluorescent signal of the first cluster group 18A passes through the mask hole 42. In the state of (c) of FIG. 12, the optical detector 50 detects the fluorescent signal for the first cluster group 18A.

Referring to (d) of FIG. 12, a head unit 40 is located relative to the flow cell 10 so that the fluorescent signal of the second cluster group 18B passes through the mask hole 42. In the state of (d) of FIG. 12, the optical detector 50 detects the fluorescent signal for the second cluster group 18B.

The inflow of the signal from the adjacent well 18 in addition to the fluorescent signal from the corresponding well 18 to the corresponding detecting element 52 is prevented or minimized by the mask holes 42 of the optical mask 40. Further, according to the exemplary embodiment of FIGS. 10 and 11, the efficient and rapid detection of the fluorescent signal may also be performed on the cluster having the more integrated pattern than the detecting element 52.

Next, a successive optical analysis method according to an exemplary embodiment of the present invention will be described.

Figure 13:
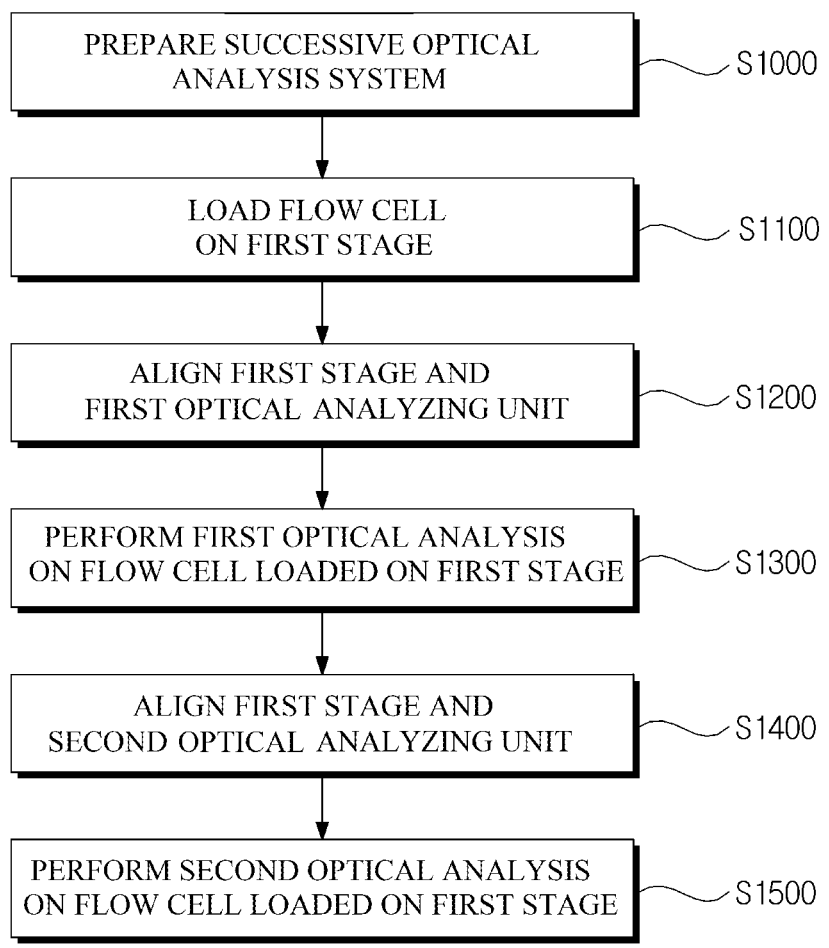
FIG. 13 is a flowchart illustrating a successive optical analysis method according to an exemplary embodiment of the present invention.

FIG. 13 is a flowchart illustrating a successive optical analysis method according to an exemplary embodiment of the present invention.

First, a successive optical analysis system 1, 1A, 1B, and 1C is prepared (S1000).

A flow cell 10 is loaded on the first stage 200a (S1100).

The first stage 200a is located and aligned within the first optical analyzing unit 100a by conveying at least one of the first stage 200a and the first optical analyzing unit 100a (S1200).

The first optical analyzing unit 100a performs a first optical analysis on the flow cell 10 loaded on the first stage 200a (S1300). As an example, the first optical analysis may be a detection of a fluorescent signal by adenine (A).

When operation S1300 is completed, the first stage 200a is located and aligned within the second optical analyzing unit 100b by conveying at least one of the first stage 200a and the second optical analyzing unit 100b (S1400).

The second optical analyzing unit 100b performs a second optical analysis on the flow cell 10 loaded on the first stage 200a (S1300). The second optical analysis may be different from the first optical analysis. As an example, in the case where the first optical analysis detects a fluorescent signal by adenine (A), the second optical analysis may detect a fluorescent signal by cytosine (C).

When the third optical analyzing unit 100c and the fourth optical analyzing unit 100d are further provided and a third optical analysis and a fourth optical analysis by the third optical analyzing unit 100c and the fourth optical analyzing unit 100d are further required, the operations similar to operations S1200 to S1500 may be further performed in the third optical analyzing unit 100c and the fourth optical analyzing unit 100d.

The process may be performed even on another added flow cell 10 in the same manner. In this case, another flow cell 10 may be loaded on the second stage 200a, so that a successive optical analysis may be performed.

As an example, in the exemplary embodiment illustrated in FIG. 2 or 3, the flow cell 10 may be loaded on each of the first to fourth stages 200a, 200b, 200c, and 200d, and the optical analysis may sequentially progress while the first stage 200a rotates in the counterclockwise direction in an order from the first optical analyzing unit 100a to the fourth optical analyzing unit 100d, the second stage 200b rotates in the counterclockwise direction in an order from the second optical analyzing unit 100b to the first optical analyzing unit 100a, the third stage 200d rotates in the counterclockwise direction in an order from the third optical analyzing unit 100c to the second optical analyzing unit 100b, and the fourth stage 200d rotates in the counterclockwise direction in an order from the fourth optical analyzing unit 100d to the third optical analyzing unit 100c.

In the exemplary embodiment, the successive optical analysis may be performed while the flow cell is sequentially loaded on the first to fourth stages 200a, 200b, 200c, and 200d. In addition, a new reagent may be supplied to the flow cell 10 after performing the successive optical analysis or before at least one of the first to fourth optical analysis.

Taking the exemplary embodiment illustrated in FIG. 4 as an example, the flow cell 10 may be loaded on the idle stage 200e or a reagent may be supplied while the optical analysis progresses for the flow cells 10 loaded on other stages 200a to 200d.

Although the exemplary embodiment of the present invention has been described for illustrative purposes, those skilled in the art will appreciate that various modifications, additions and substitutions are possible, without departing from the scope and spirit of the invention. Therefore, the embodiments disclosed in the present invention and the accompanying drawings are not intended to limit the technical spirit of the present invention, but are intended to illustrate the scope of the technical idea of the present invention, and the scope of the present invention is not limited by the embodiment and the accompanying drawings. The scope of the present invention shall be construed on the basis of the accompanying claims in such a manner that all of the technical ideas included within the scope equivalent to the claims belong to the scope of the present invention.

As described above, the exemplary embodiments have been described and illustrated in the drawings and the specification. The exemplary embodiments were chosen and described in order to explain certain principles of the invention and their practical application, to thereby enable others skilled in the art to make and utilize various exemplary embodiments of the present invention, as well as various alternatives and modifications thereof. As is evident from the foregoing description, certain aspects of the present invention are not limited by the particular details of the examples illustrated herein, and it is therefore contemplated that other modifications and applications, or equivalents thereof, will occur to those skilled in the art. Many changes, modifications, variations and other uses and applications of the present construction will, however, become apparent to those skilled in the art after considering the specification and the accompanying drawings. All such changes, modifications, variations and other uses and applications which do not depart from the spirit and scope of the invention are deemed to be covered by the invention which is limited only by the claims which follow.

What is claimed is:

1. A successive optical analysis system for optically analyzing a flow cell, comprising:
    at least one stage on which a flow cell is loaded;
    at least two optical analyzing units configured to optically analyze the flow cell loaded on the at least one stage; and
    a conveying unit configured to convey the at least one stage or at least one of the at least two optical analyzing units and align positions of one of the at least one stage and one of the at least two optical analyzing units,
    wherein each of the at least two optical analyzing units includes: a light source which emits light; an optical filter which allows an optical signal of a specific wavelength band to pass through; and an optical detector which detects the optical signal,
    wherein each of the at least two optical analyzing units further includes an optical mask in front of the optical detector, the optical mask provided with mask holes formed through the optical mask, the mask holes respectively aligned with detecting elements of the optical detector to form mask hole and detecting element combinations,
    wherein a number of reaction regions of the flow cell existing in a region photographable by the optical detector one time is more than a number of the mask hole and detecting element combinations,
    wherein the reaction regions of the flow cell are divided into first cluster group columns alternating respectively with a second cluster group columns, and
    wherein a second cluster group column is optically analyzed after a first cluster group column is optically analyzed by shifting an assembly of the optical detector and the optical mask.

2. The successive optical analysis system of claim 1, wherein the at least one stage includes a first stage and a second stage, and the second stage is positioned in a second optical analyzing unit of the at least two optical analyzing units and performs a second optical analysis while the first stage is positioned in a first optical analyzing unit of the at least two optical analyzing units and performs a first optical analysis.

3. The successive optical analysis system of claim 1, wherein the conveying unit includes a first conveying unit which conveys the at least one stage to at least one of the at least two optical analyzing units by rotating the at least one stage.

4. The successive optical analysis system of claim 1, wherein the at least one stage is position-movable by moving in at least one straight direction or rotating by a linear motor method or a piezo method.

5. The successive optical analysis system of claim 1, wherein at least one of the at least one stage and the at least two optical analyzing units moves in a vertical direction to adjust a gap between the flow cell loaded to the at least one stage and one of the at least two optical analyzing units.

6. The successive optical analysis system of claim 1, wherein the conveying unit includes a second conveying unit which conveys at least one of the at least two optical analyzing units to the at least one stage by rotating the at least two optical analyzing units.

7. The successive optical analysis system of claim 1, wherein the conveying unit includes a conveying track, and a moving conveying unit which moves the at least one stage or the at least two optical analyzing units while moving along the conveying track.

8. The successive optical analysis system of claim 1, wherein in the at least two optical analyzing units, at least one of a wavelength band of the light source, a transmissive wavelength band of the optical filter, and a transmissive wavelength band of a light source filter provided at a light output side of the light source is set differently.

9. The successive optical analysis system of claim 1, wherein a size of each of the mask holes is smaller than a size of each of the detecting elements, and is smaller than a size of a reaction region of the flow cell.

10. The successive optical analysis system of claim 1, further comprising:
    an analysis support unit which loads or unloads the flow cell for the at least one stage or supplies a reagent to the flow cell.

11. The successive optical analysis system of claim 10, wherein the analysis support unit loads or unloads the flow cell or supplies the reagent to the flow cell for one of the at least one stage that is not positioned in the at least two optical analyzing units.

12. The successive optical analysis system of claim 1,
    wherein each of the at least two optical analyzing units is further provided with a spacing to which one of the at least one stage is to move and be positioned.

13. The successive optical analysis system of claim 12, wherein the spacing is formed between the light source and the optical filter.

14. A successive optical analysis method using a successive optical analysis system including at least one stage, and an optical analyzing unit including a first optical analyzing unit and a second optical analyzing unit, the successive optical analysis method comprising:
    (a) loading a flow cell on a first stage of the at least one stage;
    (b) positioning the first stage in the first optical analyzing unit by conveying at least one of the first stage and the first optical analyzing unit;
    (c) performing, by the first optical analyzing unit, a first optical analysis on the flow cell loaded on the first stage;
    (d) positioning the first stage in the second optical analyzing unit by conveying at least one of the first stage and the second optical analyzing unit; and
    (e) performing, by the second optical analyzing unit, a second optical analysis on the flow cell loaded on the first stage,
    wherein each of the first optical analyzing unit and the second optical analyzing unit further includes an optical mask in front of an optical detector, the optical mask provided with mask holes formed through the optical mask, the mask holes respectively aligned with detecting elements of the optical detector to form mask hole and detecting element combinations,
    wherein a number of reaction regions of the flow cell existing in a region photographable by the optical detector one time is more than a number of the mask hole and detecting element combinations of,
    wherein the reaction regions of the flow cell are divided into a first cluster group columns alternating respectively with second cluster group columns, and
    wherein a second cluster group column is optically analyzed after a first cluster group column is optically analyzed by shifting an assembly of the optical detector and the optical mask.

15. The successive optical analysis method of claim 14, wherein the at least one stage further includes a second stage, and the second optical analyzing unit performs a second optical analysis on the second stage while the first optical analyzing unit performs a first optical analysis on the first stage.

16. The successive optical analysis method of claim 14, wherein each of the at least one stage is provided in plural, and the flow cell is loaded or unloaded or a reagent is supplied to the flow cell for one of the at least one stage on which an optical analysis is not performed.

17. The successive optical analysis method of claim 14, wherein the optical analyzing unit further includes a third optical analyzing unit for a third optical analysis and a fourth optical analyzing unit for a fourth optical analysis, and the first to fourth optical analyses are sequentially performed on the flow cell loaded on the at least one stage and a new reagent is supplied after performing the successive optical analysis or before at least one of the first to fourth optical analysis.

* * * * *